United States Patent [19]

Bounds

[11] 4,451,675

[45] May 29, 1984

[54] PREPARATION OF ALKYLIDENEBIS(DIBROMOPHENOL)

[75] Inventor: Charles T. Bounds, Magnolia, Ark.

[73] Assignee: The Dow Chemical Company, Midland, Mich.

[21] Appl. No.: 398,747

[22] Filed: Jul. 16, 1982

[51] Int. Cl.³ .................... C07C 39/16; C07C 37/62
[52] U.S. Cl. .................... 568/726; 568/728; 568/779
[58] Field of Search .......... 568/726, 728, 779

[56] References Cited

U.S. PATENT DOCUMENTS

| | | | |
|---|---|---|---|
| 3,029,291 | 4/1962 | Dietzler | 568/726 |
| 3,143,575 | 8/1964 | Bryner et al. | 260/619 |
| 3,182,088 | 5/1965 | Hennis | 568/726 |
| 3,234,289 | 2/1966 | Hennis | 568/726 |
| 3,299,000 | 1/1967 | Jackson et al. | 260/47 |
| 3,363,007 | 1/1968 | Majewski et al. | 568/726 |
| 3,546,302 | 12/1970 | Asadorian et al. | 260/619 |
| 3,868,423 | 2/1975 | Montanari et al. | 568/726 |
| 4,013,728 | 3/1977 | Brackenridge | 260/619 A |
| 4,112,242 | 9/1978 | Swietoslawki et al. | 568/726 |

FOREIGN PATENT DOCUMENTS 614235 12/1948 United Kingdom .

*Primary Examiner*—Warren B. Lone
*Attorney, Agent, or Firm*—Norman L. Sims

[57] ABSTRACT

The invention is a process for preparing alkylidenebis(-dibromophenol) comprising (a) dissolving alkylidenediphenol in between about 17 and 25 moles of methanol for each mole of alkylidenediphenol wherein the methanol has less than 5 percent by weight of water therein;

(b) adding to the solution between about 4.0 and 4.1 moles of bromine per mole of alkylidenediphenol at an elevated temperature;

(c) adding water to precipitate the alkylidenebis(dibromophenol) remaining in solution after the addition of the bromine in step (b) is completed; and (d) separating the alkylidenebis(dibromophenol) from the methanol solution.

11 Claims, No Drawings

PREPARATION OF ALKYLIDENEBIS(DIBROMOPHENOL)

BACKGROUND OF THE INVENTION

The invention pertains to an improved process for preparing tetrabromobisphenols and the co-product methyl bromide. The term "bisphenols", as used herein, means the binuclear phenolic compounds among which are 4,4'-methylenediphenol; 4,4'-ethylidenediphenol; 4,4'-isopropylidenediphenol; 4,4'-isobutylidenediphenol; 4,4'-sec-butylidenediphenol; and 4,4'-dihydroxydiphenyl.

Bisphenols are widely used in the chemical art and especially to react with epichlorohydrin under suitable conditions in the manufacture of epoxy resins. Bisphenols can be reacted with phosgene or diphenyl carbonates to produce polycarbonates. Halogenated bisphenols, and most especially, tetrabromobisphenols, produce epoxy resins that are resistant to burning. Tetrabromobisphenols are further useful as precursors in the manufacture of clear plastics.

Methyl bromide is a valuable commodity having a large number of known uses, e.g., as a chemical intermediate, as a fumigant and the like.

A number of attempts have been made to make tetrabromobisphenol in satisfactory high yields in a sufficiently pure state for general use as an intermediate, e.g., in the manufacture of epoxy resins, or for use in polycarbonates. It is desirable that the tetrabromobisphenols prepared be clear. Low color is desirable from an aesthetic point of view in epoxy resin use and necessary in clear plastic applications.

Color in tetrabromobisphenols is caused by impurities. Present processes for preparing tetrabromobisphenols suffer from problems of impurities and resultant color in the product.

Tetrabromobisphenols have been prepared by mixing bromine with bisphenol in a suitable reaction vessel, or by mixing bromine with bisphenol dissolved in an organic solvent, e.g., a lower alkanol, and in such organic solvents mixed with water. None of the above processes have been successful in eliminating impurities and color from the tetrabromobisphenol prepared.

Hennis, U.S. Pat. No. 3,182,088, teaches that bromine may be reacted with bisphenol in substantially pure methanol to prepare a tetrabromobisphenol. Water is added to the reaction mixture to precipitate the tetrabromobisphenol. Hennis teaches the addition time of the bromine should be at least about 0.5 hour, preferably at least one hour, at a temperature between about 15° C. and 35° C., preferably about 20° C. to 25° C. Thereafter, the reaction solution is held at a temperature between 18° C. and 65° C. for a time between about 0.5 and 4.0 hours. Hennis further teaches that the amount of methanol employed is not critical so long as the amount present is ample to serve as a reaction medium, e.g., between 1.0 and 2.0 parts by weight per part of bisphenol. It is also taught that use of a higher post-reaction temperature results in a product of lower purity.

It has now been discovered that the addition time for bromine can be less than 0.5 hour. It has been further discovered that the reaction can be run at a temperature above 50° C. and a higher post-heating temperature does not reduce the purity of the product. It has also been discovered that the post-heating period, although desirable, is not necessary to the production of pure colorless tetrabromobisphenol. Further, the amount of methanol used in relation to bisphenol is critical to the yield of the product and its purity. The process also requires less energy to prepare tetrabromobisphenol.

The above description of inventive features of the process disclosed herein is not exhaustive and further inventive features will be apparent from the following description.

SUMMARY OF THE INVENTION

The invention is a process for preparing alkylidenebis(dibromophenol) comprising:

(a) dissolving alkylidenediphenol in between about 17 and 25 moles of methanol for each mole of alkylidenediphenol wherein the methanol has less than about 5 percent by weight of water therein;

(b) adding to the solution between about 4.0 and 4.1 moles of bromine per mole of alkylidenediphenol at an elevated temperature;

(c) adding water to precipitate the alkylidenebis(dibromophenol) remaining in solution after the addition of the bromine in step (b) is completed; and (d) separating the alkylidenebis(dibromophenol) from the methanol solution.

The process optionally may further include holding the solution of alkylidenediphenol in methanol at elevated temperatures for up to an hour, after the addition of the bromine to the solution has been completed. The process may further include condensing any methanol vaporized and collecting the coproduct methyl bromide evolved. The process may also further include washing the alkylidenebis(dibromophenol) with a solution of methanol in water. This process prepares tetrabromobisphenols in higher purity with lower color than any of the above-described processes.

DETAILED DESCRIPTION OF THE INVENTION

This process coproduces tetrabrominated bisphenols and methyl bromide. The following equations demonstrate how this coproduction occurs. Equation I demonstrates the preparation of tetrabromobisphenol.

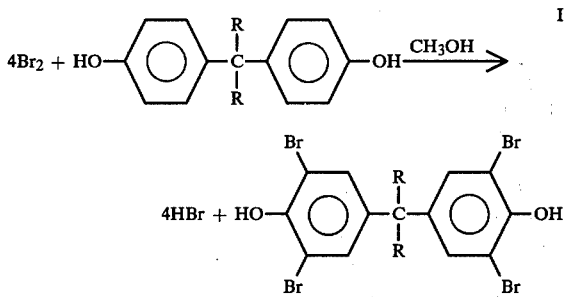

In equation I, R is independently in each occurrence a $C_{1-4}$ alkyl group, preferably methyl. In the preferred embodiment the starting bisphenol is isopropylidenediphenol, bisphenol A, and the product is isopropylidenebis(dibromophenol), tetrabromobisphenol A. The hydrogen bromide produced in the above-described reaction dissolves in the methanol solvent and reacts with methanol to form methyl bromide. This reaction is described in equation II.

$$CH_3OH + HBr \rightleftharpoons CH_3Br + H_2O \tag{II}$$

The solvation of hydrogen bromide in methanol is exothermic. The heat generated is sufficient to drive the temperature of the reaction solution up to the reflux temperature of methanol. In the process disclosed herein, the reaction is allowed to run at the reflux temperature of methanol, about 65° C. The prior art teaches the reaction should be run at between 15° C. and 35° C. In order to run the reaction at such temperatures, the reaction solution has to be cooled usually by some means of refrigeration. This requires a significant amount of energy. By allowing the reaction to run without cooling by some means of refrigeration, a significantly lower amount of energy is required.

The tetrabromobisphenol produced as described in equation I is soluble in methanol but its solubility is very sensitive to the amount of water in the reaction solution. As hydrogen bromide and methanol react, as described in equation II, water is produced. As the concentration of water increases, some of the tetrabromobisphenol precipitates.

In the claimed process, methanol is charged to a reaction vessel in an amount between about 17 and 25 moles of methanol per mole of bisphenol to be brominated. The use of too little methanol results in premature precipitation of an impure tetrabromobisphenol having a lowered melting point. It is desirable to use as little methanol as possible for several reasons. As methyl bromide is soluble, the use of excess methanol reduces the amount of methyl bromide co-product recovered. Also, the use of excess methanol can increase production costs by increasing the cost of solvent energy recovery and the size of the reactor required.

The methanol used should have less than about 5 percent by weight of water therein, preferably less than 2 percent water. Those bisphenols which have not been completely brominated to the tetrabrominated species are also sensitive to the amount of water in the reaction solution. Where the initial water concentration is too high, these less brominated species will being to precipitate before all of the bromine is added resulting in lower purity in the tetrabromobisphenols produced. By using methanol with less than about 2 percent by weight of water therein, precipitation of underbrominated bisphenol species can be avoided.

In one embodiment, once the methanol has been charged to the reactor, the bisphenol is dissolved therein. At this time it is desirable to begin rapid agitation of the solution.

Between 4.0 and 4.1 moles of bromine are added to the solution. The use of excess bromine beyond a stoichiometric amount has been found unnecessary and the use of less than that amount results in underbromination. It has been discovered that it is advantageous to add the bromine rapidly. The only limit is that addition should not be so rapid as to carry bromine vapors through any reflux condenser used in the process. It is preferable that addition times be less than about 0.5 hour, more preferably less than about 0.25 hour. Lower addition times have been found to produce products with significantly less color, less by-products and a product with a higher melting point.

This reaction can be run at a temperature of between about −95° C. and 200° C. Above 50° C. gives good results and between about 60° C. and 65° C. gives better results. 65° C. is about the reflux temperature of methanol. At temperatures above 65° C. the pressure must be increased to keep the reaction mixture at reflux. This process can be run at atmospheric and super atmospheric temperatures. The product has significantly less color where higher temperatures are used.

It is desirable to use a reflux condenser over the reaction pot to condense the methanol volatilized to prevent the amount of methanol in the reaction vessel from getting too low. Such a condenser should be sized to condense the methanol and allow the methyl bromide produced to pass through to another condenser which operates at a lower temperature. The condenser is preferably kept at a temperature between 5° C. and 8° C. which allows the methyl bromide to pass and condenses methanol.

Once the bromine addition has been completed, the formation of significant hydrogen bromide and its solvation in methanol stops, resulting in a lowering of the reaction temperature. At this point, the reaction solution can be heated by external means. This optional heating is advantageous as the reaction described in equation II is an equilibrium reaction, which requires heat to increase the formation of the products methyl bromide and water. A continued period of heating increases the yield of methyl bromide. Further, increasing the amount of water in solution results in further precipitation of the tetrabromobisphenol. It has been found that when post-heating is used, the crystals formed by the precipitation are of increased quality and larger. A post-heat period of about 3.0 hours or less is suitable. Twenty minutes has been found to result in a very good product. The post-heat period is not necessary in the production of tetrabromobisphenols, the only advantage is the production of larger crystals.

The above-described Hennis patent calls for a post-addition heating period wherein the temperature used would be up to 65° C. The process claimed herein further saves energy in that the reaction solution is already near or at that temperature when the addition of bromine is complete, whereas the above-described process requires the solution to be heated to the post-addition heating temperature. Thus less energy is required for any post-heat period than is required by such process. Post-heat period means herein that period of heating after the addition of bromine and before the addition of water to precipitate the tetrabromobisphenol A prepared.

The rate of agitation should be reduced during any post-heat period to a rate which is just sufficient to keep the precipitated products in dispersion. It is believed excessive agitation at this time interferes with crystal growth.

As the methyl bromide is formed, it dissolves in methanol. When the methanol becomes saturated the methyl bromide formed volatilizes and can be collected. Because of the solvation in methanol, the practical upper limit of methyl bromide yield is 80 percent. It should be noted that in order to optimize the yield of methyl bromide recovered, a period of post-heating is necessary.

To recover the tetrabromobisphenol which remains in the methanol solution, water is added to precipitate the product. It is preferable to add sufficient water so that the reaction solution has approximately a 1:1 molar ratio of methanol to water. If too little water is added, the yield of product recovered is too low. If too much water is used, the product recovered has too many impurities and an unacceptable color.

The precipitated product can be recovered from the reaction by conventional means, including filtration.

It is desirable to wash the recovered tetrabromobisphenol with a water-methanol solvent. It is preferable that the solvent be 50 percent by volume methanol in water. This washing removes impurities which add color and can cause degradation of the product. It is desirable thereafter to wash the product with water to remove any methanol associated with the product, as methanol is flammable under some drying conditions.

It is not necessary to dry the tetrabromobisphenol. It is desirable to heat the product to evaporate the water so the product will be free-flowing. Drying for extended times or at excessive temperatures should be avoided.

The tetrabromobisphenols produced by this process have significantly lower color numbers than those produced by the method described in the Background of the Invention. Tetrabromobisphenols with lower color numbers are preferred in industrial uses and substantially clear ones are required for uses in clear plastic. The color numbers used herein correspond to those used by the APHA. The procedure used for determining the color numbers corresponds to ASTM procedure D-1209 "Color of Clear Liquids (Platinum-Cobalt Scale)".

Having disclosed and described the invention herein the following examples are given to describe the invention and are not intended to limit the scope of the invention described.

SPECIFIC EMBODIMENTS

Apparatus

The reactor used was a 3-liter glass jacketed pot. The jacket allowed heated or cooled heat-exchange fluid to be circulated around the reactor without obscuring the contents of the reactor. The reactor was equipped with a thermometer, a variable speed stirrer and a 250-ml dropping funnel. The dropping funnel was modified with a polytetrafluoroethylene (PTFE) dip-pipe which allowed bromine to be introduced into the reactor wall and slightly above the rotating PTFE stirrer blades. The reactor was fitted with an adaptor and a vertical condenser, which operated as a partial condenser. The adaptor had connected to it a second dropping funnel, used to introduce precipitating water into the reflux. The adaptor was also equipped with a sampling point which was used to withdraw samples of the condensate and to divert condensate flow from the reactor. The partial condenser was connected to a second adaptor, also equipped with a thermometer, which turned up-flowing vapors and directed them down onto the bottom of a cold finger condenser loaded with dry ice/acetone. Condensed product flowed downward into a graduated cylinder immersed in an ice bath, which allowed the amount of methyl bromide collected to be monitored.

EXAMPLE 1

The reactor was charged with 20 moles of methanol and 1.00 mole of para-bisphenol A (4,4'-isopropylidenediphenol), which was stirred to dissolve the para-bisphenol A. With continued vigorous stirring, 4.05 moles of bromine were added subsurface over a period of 60 minutes, while maintaining the reactor temperature at 30° C. Thereafter, the contents of the reactor were stirred for 30 minutes. Then the reactor temperature was raised to the solvent reflux temperature for about 150 minutes. Throughout this process the methyl bromide evolved was collected. Water was added until the ratio of methanol to water in the reactor was 1:1, so as to precipitate the product. This mixture was refluxed for about 25 minutes. The reactor was cooled and the product collected by vacuum on a filter. The product was washed with a solution of 50 percent by volume of methanol, then with water. The product was dried under vacuum at about 100° C.

A 97 percent yield of polycarbonate grade tetrabromobisphenol A with a melting point of 182° C. and an APHA color number of 22 was obtained along with a 74 percent yield of methyl bromide.

EXAMPLE 2

The process of Example 1 was run with a bromination time of 6 minutes. The reactor was not cooled. A 96 percent yield of tetrabromobisphenol A was recovered. The melting point was 183° C. with a color number of 11.

EXAMPLE 3

The process of Example 1 was run with a bromination time of 29 minutes. The reactor was not cooled. A 96 percent yield of tetrabromobisphenol A was recovered. The melting point was 180° C. with a color number of 12.

EXAMPLE 4

An experiment similar to Example 1 was run except the reaction time was 123 minutes and the reaction temperature was 50° C. The tetrabromobisphenol A produced had a melting point of 182 and a color number of 26. The color number is much higher than that in Example 2.

The results of Examples 1-4 are compiled in Table I.

TABLE I

| Bromination Example | Time, Min. | Yield | M.P. | Color | Reaction Temp. °C. |
|---|---|---|---|---|---|
| 1 | 60 | 97 | 182 | 22 | 65 |
| 2 | 6 | 96 | 183 | 11 | 65 |
| 3 | 29 | 96 | 180 | 12 | 65 |
| 4 | 123 | 97 | 182 | 26 | 50 |

Table I demonstrates that faster addition times result in a better color number.

EXAMPLE 5

Four experiments like Example 1 were run where the amount of water added to precipitate the tetrabromobisphenol A was varied and the bromination times were between 6 and 29 minutes. The reactor was not cooled. The results are compiled in Table II.

TABLE II

| Example | * | % Yield | Melting Point | Methanol Color | Bromination Time (min) |
|---|---|---|---|---|---|
| 5a | 6.25:1 | 81 | 183 | 8 | 11 |
| 5b | 2.83:1 | 87 | 183 | 10 | 7 |
| 5c | 1:1 | 96 | 183 | 11 | 6 |
| 5d | 0.41:1 | 99 | 182 | 146 | 29 |

*Final Molar Ratio Methanol/Water.

Table II demonstates that addition of too much water significantly increases the color number, whereas addition of an insufficient amount results in poor yields.

EXAMPLE 6

Four experiments like Example 1 were run where the amount of water in the methanol solvent was varied and the bromination times were between 6 and 30 minutes. The reactor was not cooled.

Further the post-addition heating period continued until a 64 percent yield of methyl bromide was collected. The results are compiled in Table III.

TABLE III

| Example | Water Added % | Yield % | M.P. | Color | * | Bromination Time (min) |
|---|---|---|---|---|---|---|
| 6a | 0 | 96 | 180 | 12 | 35 | 29 |
| 6b | 2 | 96 | 181 | 12 | 45 | 30 |
| 6c | 10 | 96 | 178 | 15 | 150 | 15 |
| 6d | 0 | 96 | 183 | 11 | 45 | 6 |

*Approximate time in minutes to achieve a 64% yield of $CH_3Br$.

Table III shows that 10 percent water in the methanol results in a less pure product, as evidenced by the lower melting point. It further lengthens the time necessary to produce and collect a desired amount of methyl bromide. Table III further shows that 2 percent water in the methanol solvent does not harm the products.

EXAMPLE 7

Three experiments like Example 1 were run where the methanol to para-bisphenol A ratio was changed. The bromination times were between 17 and 30 minutes. The reactor was not cooled. The results are shown in Table IV.

TABLE IV

| Example | * | Yield % | Melting Point | Methanol Color | Bromination Time (min) |
|---|---|---|---|---|---|
| 7a | 20.0/1.00 | 96 | 182 | 11 | 30 |
| 7b | 17.0/1.00 | 97 | 181 | 11 | 24 |
| 7c | 15.0/1.00 | 97 | 180 | 13 | 17 |

*Methanol/PB-A Ratio.

Table IV shows that the color number is higher and the purity of the product is lower, where the ratio of methanol to para-bisphenol A is 15:1.

EXAMPLE 8

Four experiments like Example 1 were run except the post-addition heating step was altered. The bromination times were between 9 and 30 minutes. The results are compiled in Table V.

TABLE V

| Example | Post-addition heating step | % Yield | M.P. | Color | Bromination Time (min) |
|---|---|---|---|---|---|
| 8a | Post heat, 20 min. at reflux | 97 | 183 | 14 | 9 |
| 8b | No post heat | 97 | 183 | 15 | 13 |
| 8c | Post heat, 20 min. at reflux | 97 | 181 | 11 | 29 |
| 8d | No post heat | 96 | 181 | 7 | 30 |

Table V shows that a good product can be achieved with no post heat.

What is claimed is:

1. A process for preparing alkylidenebis(dibromophenol) comprising
   (a) dissolving alkylidenediphenol in between about 17 and 25 moles of methanol for each mole of alkylidenephenol wherein the methanol has less than about 5 percent by weight of water therein;
   (b) adding to the solution between about 4.0 and 4.1 moles of bromine per mole of alkylidenediphenol at an elevated temperature wherein the bromine is added over a time period of less than about 0.5 hours;
   (c) adding water to precipitate the alkylidenebis(dibromophenol) remaining in solution after the addition of the bromine in step (b) is completed;
   (d) separating the alkylidenebis(dibromophenol) from the methanol solution wherein the alkylidenebis(dibromophenol) prepared has an APHA color number of 20 or less.

2. The process of claim 1 which further includes holding the solution of alkylidenediphenol in methanol at elevated temperatures for up to about 3.0 hours, after the addition of the bromine to the solution has been completed.

3. The process of claim 1 or 2 which further includes condensing any methanol vaporized and collecting methyl bromide evolved.

4. The process of claim 1 wherein the addition time is less than about 0.25 hour.

5. The process of claim 1 which further includes washing the separated alklidenebis(dibromophenol) with a solution of methanol in water.

6. The process of claim 5 wherein the solution used to wash the alkylidenebis(dibromophenol) is 50 volume percent methanol in water.

7. The process of claim 1 wherein the methanol in which the alkylidenephenol is dissolved has about 2 percent by weight, or less, of water therein.

8. The process of claim 1 wherein the temperature is above 50° C.

9. The process of claim 8 wherein the temperature is between 60° C. and 65° C.

10. The process of claim 1 wherein, in step (c), water is added until the final molar ratio of water to methanol in the solution is about 1:1.

11. The process of claim 1 wherein the alkylidenebis(dibromophenol) produced is 4,4'-isopropylidenebis(2,6-dibromophenol).

* * * * *

UNITED STATES PATENT AND TRADEMARK OFFICE
CERTIFICATE OF CORRECTION

PATENT NO. : 4,451,675
DATED : May 29, 1984
INVENTOR(S) : Charles T. Bounds

It is certified that error appears in the above—identified patent and that said Letters Patent is hereby corrected as shown below:

Col. 1, line 50, "about" should be deleted.

Col. 3, lines 31,32, "en-ergy" should be deleted.

Col. 3, line 39, "being" should read -- begin --.

Col. 5, line 14, "method" should read --methods --.

Col. 8, lines 19,20, "al-kylidenephenol" should read -- al-kylidenediphenol --.

Col. 8, line 29, "completed;" should read --completed; and --.

Col. 8, line 45, "alklidenebis(dibromophenol) should read -- alkylidenebis(dibromophenol) --.

Col. 8, line 50, "alkylidenephenol" should read -- alkylidenediphenol --.

Signed and Sealed this

Sixth Day of November 1984

[SEAL]

Attest:

GERALD J. MOSSINGHOFF

Attesting Officer

Commissioner of Patents and Trademarks